(12) United States Patent
Bourlon et al.

(10) Patent No.: US 10,605,791 B2
(45) Date of Patent: Mar. 31, 2020

(54) DEVICE FOR TAKING AND ANALYZING A GASEOUS SAMPLE

(71) Applicant: Commissariat a l'energie atomique et aux energies alternatives, Paris (FR)

(72) Inventors: Bertrand Bourlon, Saint Martin le Vinoux (FR); Jean-Francois Beche, Montbeliard (FR); Florence Ricoul, Quaix en Chartreuse (FR); Bruno Truong, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 248 days.

(21) Appl. No.: 15/617,517

(22) Filed: Jun. 8, 2017

(65) Prior Publication Data

US 2017/0356886 A1 Dec. 14, 2017

(30) Foreign Application Priority Data

Jun. 9, 2016 (FR) ...................................... 16 55295

(51) Int. Cl.
| | |
|---|---|
| *G01N 30/06* | (2006.01) |
| *G01N 1/22* | (2006.01) |
| *G01N 35/10* | (2006.01) |
| *G01N 30/08* | (2006.01) |

(Continued)

(52) U.S. Cl.
CPC ............ *G01N 30/06* (2013.01); *G01N 1/2214* (2013.01); *G01N 1/405* (2013.01); *G01N 30/08* (2013.01);
(Continued)

(58) Field of Classification Search
CPC .. G01N 30/02; G01N 2030/025; G01N 30/04; G01N 30/06; G01N 30/08;
(Continued)

(56) References Cited

U.S. PATENT DOCUMENTS

| | | | | |
|---|---|---|---|---|
| 3,174,327 A | * | 3/1965 | Hansen ..................... | G01N 7/00 73/25.05 |
| 6,223,584 B1 | * | 5/2001 | Mustacich ............. | G01N 1/405 250/288 |

(Continued)

FOREIGN PATENT DOCUMENTS

| | | |
|---|---|---|
| WO | WO 2008/021275 A2 | 2/2008 |
| WO | WO 2012/109237 A1 | 8/2012 |

OTHER PUBLICATIONS

French Preliminary Search Report dated Feb. 15, 2017 in French Application 16 55295 filed on Jun. 9, 2016 (with English Translation of Categories of Cited Documents and Written Opinion).

*Primary Examiner* — Benjamin R Schmitt
(74) *Attorney, Agent, or Firm* — Oblon, McClelland, Maier & Neustadt, L.L.P.

(57) ABSTRACT

A device for analyzing a gaseous sample including a first housing including a detection assembly housed in the housing including a preconcentrator, a chromatography column and a detector intended to detect the presence of the separated compounds, a sampling assembly including a cartridge that is removable relative to the first housing, a control and processing unit housed in the housing and configured to execute an analysis operating mode capable of generating a first command for the detection assembly to analyze a first gaseous sample, a second command to determine the exceeding of at least one alert threshold and, if an alert threshold is exceeded, a third command for the sampling assembly to take a second gaseous sample.

11 Claims, 3 Drawing Sheets

(51) Int. Cl.
  *G01N 1/40* (2006.01)
  *G01N 30/30* (2006.01)
  *G01N 30/88* (2006.01)
  *G01N 1/20* (2006.01)
  *G01N 30/16* (2006.01)
  *G01N 30/02* (2006.01)

(52) U.S. Cl.
  CPC ............. *G01N 30/30* (2013.01); *G01N 30/88* (2013.01); *G01N 35/1095* (2013.01); *G01N 30/16* (2013.01); *G01N 2001/2071* (2013.01); *G01N 2001/2291* (2013.01); *G01N 2030/025* (2013.01); *G01N 2030/062* (2013.01); *G01N 2030/3061* (2013.01); *G01N 2030/8804* (2013.01)

(58) Field of Classification Search
  CPC .... G01N 30/20; G01N 30/30; G01N 35/1095; G01N 2001/2071; G01N 2030/3061

USPC .................. 73/23.35, 23.36, 23.4, 23.41
  See application file for complete search history.

(56) References Cited

U.S. PATENT DOCUMENTS

| | | |
|---|---|---|
| 2007/0266858 A1 | 11/2007 | Alm et al. |
| 2008/0064113 A1* | 3/2008 | Goix .................. G01N 35/1095 436/86 |
| 2008/0148815 A1 | 6/2008 | Lucas et al. |
| 2009/0090197 A1* | 4/2009 | Finlay .................. G01N 1/2214 73/863.12 |
| 2009/0223310 A1 | 9/2009 | Syage et al. |
| 2010/0250146 A1 | 9/2010 | Alm et al. |
| 2010/0307224 A1 | 12/2010 | Lucas et al. |
| 2012/0223226 A1 | 9/2012 | Rafferty et al. |
| 2015/0010442 A1 | 1/2015 | Rafferty et al. |

* cited by examiner

DEVICE FOR TAKING AND ANALYZING A GASEOUS SAMPLE

TECHNICAL FIELD OF THE INVENTION

The present invention relates to a device for analyzing a gaseous sample.

STATE OF THE ART

Air quality analysis has become an important subject, particularly for detecting pollution levels. The analyses of VOCs (volatile organic compounds) form part of the air quality analyses implemented these days, for example.

The analysis devices use a gas phase chromatography column. The gaseous sample is first of all introduced at the column head and is conveyed through the column by a vector gas. The different compounds of the gaseous sample are separated along the column according to their affinity with the standing phase. The more the compound has affinities with the standing phase, the longer it will take to leave the column. At the column outlet, the compounds separated from the sample pass into a detector responsible for assessing their quantity in the vector gas by virtue of the measurement of different physical properties. It thus generates distinct electrical signals for each compound, thus forming a chromatogram showing successive peaks.

Currently, to analyze a gaseous sample like air and detect the level of certain pollutants, it is known practice to employ a cartridge which takes the form of a glass or metal tube in which a gaseous sample to be analyzed is taken. The tube containing the sample is then brought to the laboratory for analysis. It is placed in an analysis device as described above and which makes it possible to detect the presence and the quantity of certain targeted compounds present in the sample. This analysis solution is very accurate but it requires a heavy installation and requires a certain delay before obtaining the results.

To mitigate these drawbacks, portable analysis devices have been proposed allowing for an on-site analysis of the air quality. Such is the case for example with the device described in the document US2009/223310A1.

However, most of the known devices present certain constraints, notably:
- they often require the use of a vector gas to push the sample in the chromatography column,
- the cartridges employed often have a proprietary design, which does not allow them to be compatible with other already existing analysis devices.

Moreover, in some cases, it has been noted that when the sampling window is particularly short, for example upon the presence of a cloud of toxic pollution, it may prove necessary to do both a rapid analysis in order to check for the presence of certain toxic compounds and a more in-depth analysis to detect, if necessary, the presence of other compounds.

A first aim of the invention is to propose an analysis device of portable type, which does not require the use of a vector gas to ensure the sampling and the analysis and which operates particularly efficiently, notably when the sampling window proves particularly short.

The device of the invention offers the particular feature of employing a removable sampling cartridge which is compatible both with the portable analysis device that can be used on site but also with an analysis installation present in the laboratory.

Another aim of the invention is to propose an adapter which makes it possible to use the removable cartridge of the device in an analysis installation present in the laboratory.

SUMMARY OF THE INVENTION

The first aim of the invention is achieved by a device for analyzing a gaseous sample comprising a first housing and which comprises:
- a detection assembly housed in said first housing comprising a preconcentrator intended to perform a preconcentration of the compounds to be analyzed of the gaseous sample and an injection, a chromatography column intended to separate said compounds present in said gaseous sample taken in the cartridge and a detector connected at the output of said chromatography column and intended to detect the presence of said separated compounds,
- a sampling assembly comprising a cartridge that is removable relative to said first housing, said cartridge comprising a second housing enclosing a preconcentrator intended to perform a preconcentration of the compounds to be analyzed of the gaseous sample,
- a control and processing unit housed in said first housing and configured to execute an analysis operating mode in which it is capable of generating a first command for the detection assembly to analyze a first gaseous sample, a second command to determine the exceeding of at least one alert threshold and, if an alert threshold is exceeded, a third command for the sampling assembly to take a second gaseous sample.

According to a particular feature, said cartridge comprises:
- a heating resistor,
- an electrical connector connected to said heating resistor and intended to be linked to an electrical power source to power said heating resistor,
- a fluid inlet through which said gaseous sample is sucked to the interior of the cartridge,
- a fluid outlet connected to said preconcentrator to discharge the compounds to be analyzed.

According to another particular feature, the second housing of the cartridge is produced in a metal material, or at least in a thermally resistant material.

According to another particular feature, the connector of the cartridge is formed by electrical tracks flush with said second housing.

According to another particular feature, said first housing of the device has a recess intended to receive said sampling cartridge removably.

According to another particular feature, the device comprises a pumping system arranged to suck said first gaseous sample into said detection assembly and to suck said second gaseous sample into said sampling assembly.

According to another particular feature, the device comprises a first fluid inlet connected to the detection assembly and a second fluid inlet connected to the sampling assembly.

According to another particular feature, said control and processing unit is configured to execute a cartridge reinitialization operating mode.

According to another particular feature, the detector is of the type with thermal conductivity.

According to another particular feature, the device comprises a power source comprising a removable battery and it comprises a connector incorporated in said first housing to which said battery is connected.

The invention relates also to an adapter comprising a baseplate provided with a recess intended to receive a sampling cartridge removably like that employed in an analysis device defined above, said adapter comprising:
- a connector linked to an electrical power source and intended to be connected to the connector of said cartridge to power its heating resistor,
- a fluid inlet intended to be linked on one side to a vector gas source and on the other side to the fluid inlet of said cartridge,
- a fluid outlet intended to be linked on one side to the fluid outlet of said cartridge and on the other side to the inlet of a gaseous sample analysis installation.

The invention relates also to a method for analyzing a gaseous sample, which comprises the following steps implemented using the analysis device as defined above:
- activation of the detection assembly to analyze a first gaseous sample,
- determination of the exceeding of at least one alert threshold after analysis of said first gaseous sample,
- if an alert threshold is exceeded, automatic activation of the sampling assembly to take a second gaseous sample.

BRIEF DESCRIPTION OF THE FIGURES

Other features and advantages will emerge from the following detailed description given in light of the attached drawings in which.

DETAILED DESCRIPTION OF AT LEAST ONE EMBODIMENT

The invention lies in the field of the analysis of a gas sample in order to determine the quality thereof and in particular generate an alert in the event of the excessively marked presence of one or more particularly toxic compounds. As is known, it will for example involve an air analysis of VOC type to determine the content in the air of certain volatile organic compounds, such as BTEX (benzene/toluene/ethylbenzene/xylene) or for example an analysis of the air to warn of a chemical threat (presence of sarin gas).

Hereinafter in the description, there are defined in particular the gaseous sample, for example air, which is taken from the ambient space and the compounds present in this gaseous sample and that are to be detected and analyzed.

Figure 1A:
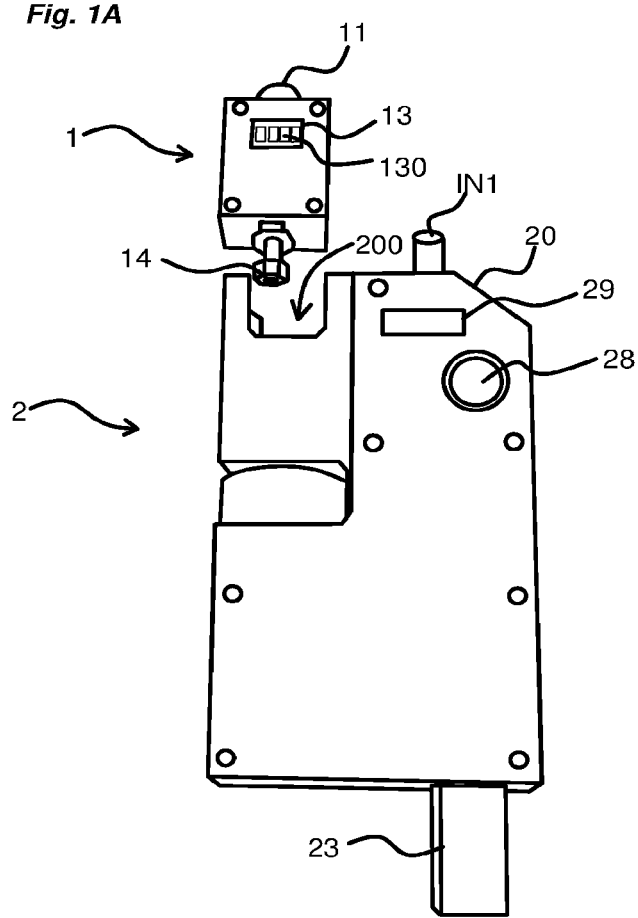
FIGS. 1A and 1B represent a perspective view of the analysis device of the invention, respectively before insertion of the cartridge and after insertion of the cartridge.
Figure 1B:
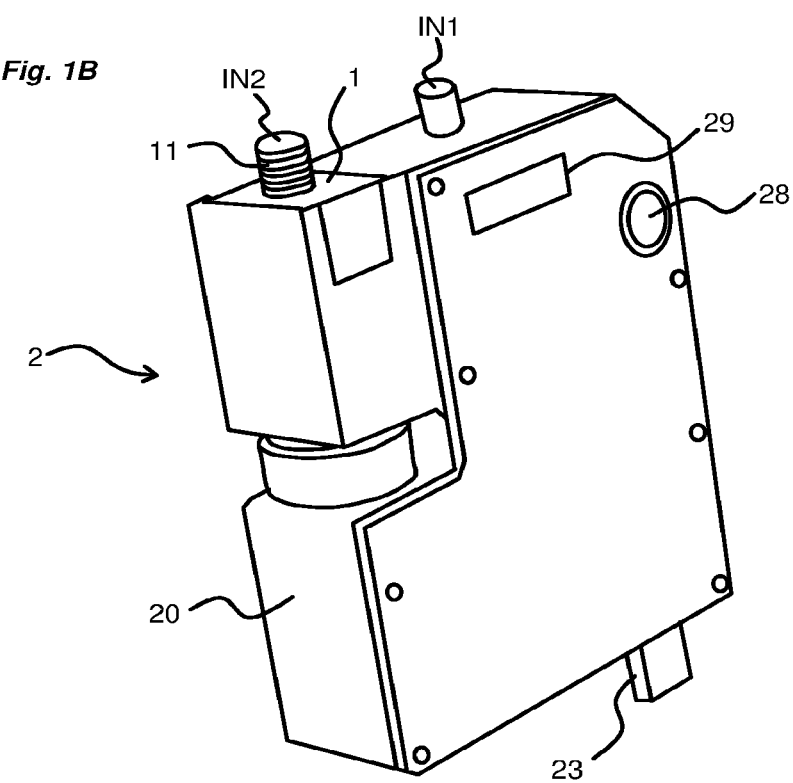
Figure 2:
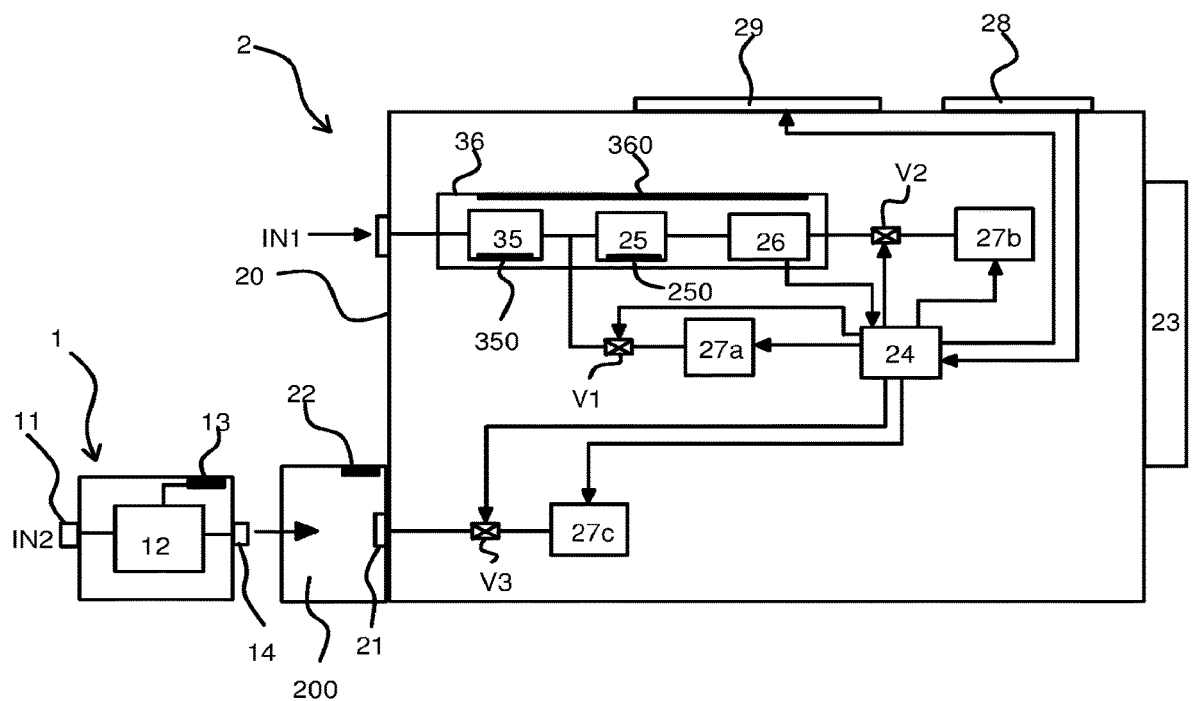
FIG. 2 schematically represents the architecture of the analysis device of the invention of FIGS. 1A and 1B.
Figure 3:
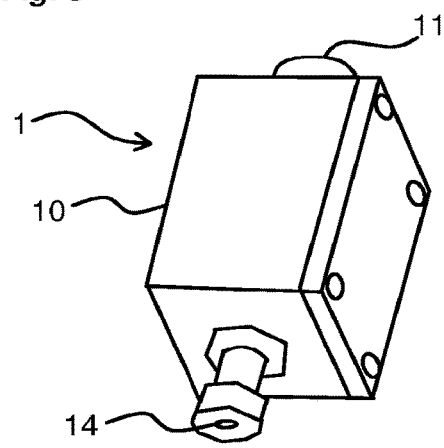
FIG. 3 represents a perspective view of the cartridge of the invention.

Referring to FIGS. 1A, 1B and 2, the analysis device 2 of the invention is configured to implement both an analysis function using a detection chain and a sampling function in a specific cartridge described hereinbelow.

The analysis device 2 comprises a housing 20.

The analysis device 2 comprises a detection assembly housed in the housing 20 and a sampling assembly housed in the same housing 20.

The analysis device advantageously comprises two distinct fluid inlets, a first fluid inlet IN1 leading to the detection assembly and a second fluid inlet IN2 leading to the sampling assembly.

The analysis device comprises a pumping system.

The device also comprises an electrical power source formed by a battery 23 connected to the housing 20 of the device 2.

Detection Assembly

The detection assembly comprises a preconcentrator 35, a gas phase chromatography column 25 connected to the preconcentrator, at the outlet thereof, and a detector 26 connected at the outlet of the column.

The preconcentrator 35 is linked directly to the first fluid inlet IN1 of the device. The preconcentrator 35 makes it possible to accumulate, using an adsorbent, the compounds to be detected that are present in the gaseous sample and makes it possible to release them by thermal desorption, under the effect of an abrupt temperature rise. An amplification of the concentration and therefore of the signal will thus be able to be obtained. A preconcentrator for example consists of a silicon microcomponent filled with at least one adsorbent (for example particles of Tenax—registered trademark) and provided with a heating resistor 350 on its bottom face. Metal or silica capillaries make it possible to ensure the circulation of the gas mixture in the device. Micropillars are arranged in front of the outlet of the preconcentrator in order to prevent the leaking of the adsorbent particles used.

The gas phase chromatography column 25 preferentially takes the form of a silicon microcolumn but can also be a capillary column used conventionally in chromatography. Such a column is well known and comprises a microscopic internal channel into which the sample taken is injected. Said column 25 is housed in the housing 20 of the device 2 and connected at the outlet of the preconcentrator. The principle of operation of such a column is well known and will not be detailed in this application. Just as a reminder, the column is provided with a standing phase by virtue of which the different compounds of the sample will be separated from one another. The standing phase creates a phenomenon of retention with the different compounds of the sample. The more affinities the compound exhibits with the standing phase, the longer it will remain in the column. The column 25 is provided with a heating device 250, powered by the battery 23 of the device and raised to a determined temperature to assist in the elution of the heaviest compounds, as well known in gas phase chromatography.

The detector 26 connected at the outlet of the column 25 is intended to detect the presence of each compound present in the sample taken. Preferentially, it will be an electrical thermal conductivity detector (TCD). Such a detector 26 is based on the Wheatstone bridge principle. The passage of the various compounds of the sample in the analysis line of the bridge having two resistances will cause the voltage to vary at the terminals of the bridge, this variation being due to the difference in conductivity of each compound. The control and processing unit 24, which will be described hereinbelow, thus receives the analog voltage variation signals and process them.

The detection assembly also comprises a heating chamber 36 insulated so as to ensure, via a heating resistor 360, the heating of the preconcentrator-column-detector analytical line. It is known in the field of analytical chemistry that, for compounds having a high molar mass or a high boiling point, it is necessary to heat the analytical line in order to ensure an effective analysis. The presence of cold points along this analytical line can lead to a widening of the chromatographic spikes, even a total condensation of the compounds at these cold points, degrading the analyses or making them impossible.

The detection assembly will advantageously be removable inside the support 20.

The preconcentrator 35 and the chromatography column 25 include their own heating means. The preconcentrator and the column have, on the rear face of the chips, their own means for heating and probing the temperature of the chips. The preconcentrator will be heated independently of the column (for example by rising to 220° C. in 10 s, and by remaining at this temperature for 5 s) so as to desorb the analytes which will have been previously preconcentrated on the adsorbent. The column will then if necessary be able to execute a thermal ramp in temperature during the separation of the compounds (for example: ramp from 80° C. to 150° C. for 1 minute).

The chromatography column 25 and the preconcentrator 35 are held in open work frames housed in the housing 20 of the device and having a low thermal conductivity so as to limit the transfers of heat between the silicon chips and their support.

Sampling Assembly

The analysis device 2 comprises a recess 200 intended to receive a removable cartridge 1. The recess 200 is accessible from the outside so as to be able to easily house the cartridge 1 therein.

The cartridge 1 comprises a housing 10 that is sealed (advantageously hermetically). The housing of the cartridge is produced in a material with high temperature resistance. It will for example be able to withstand temperatures ranging up to 200° C. or 300° C. In a nonlimiting manner, the housing 10 is for example produced in metal material and is of parallelepipedal form. The housing 10 of the cartridge will advantageously be made up of two parts, one of them being a removable cap.

The cartridge 1 comprises a fluid inlet 11 formed through its housing 10 and through which the gaseous sample is taken from the outside using the pumping system of the device of the invention. This fluid inlet 11 comprises a specific end-fitting through which the gaseous sample is sucked to the interior of the cartridge. Furthermore, this end-fitting is arranged to be connected hermetically to a corresponding end-fitting of an adapter 3 so as to be linked to a vector gas injection device. The dual functionality of the fluid inlet 11 of the cartridge will be explained hereinbelow. The different end-fittings employed are standard end-fittings.

When the cartridge is incorporated in the device, the second fluid inlet IN2 of the device corresponds to the fluid inlet 11 of the cartridge 1.

Figure 5A:
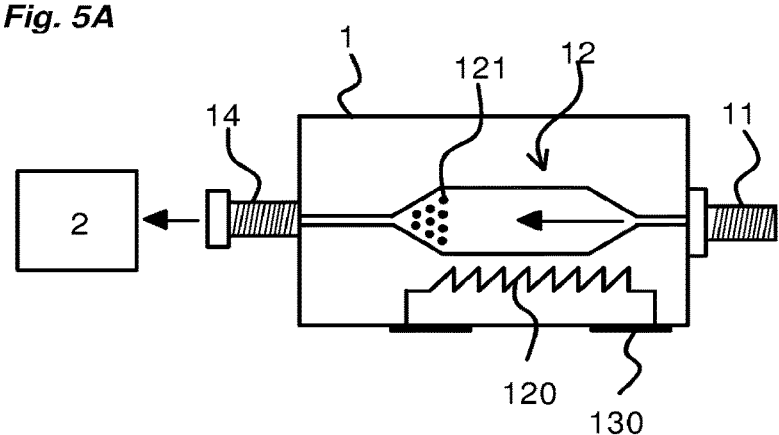
FIGS. 5A and 5B illustrate the two possible uses of the cartridge of the invention, respectively when the latter is inserted in the analysis device of the invention and when the latter is inserted in the adapter linked to an analysis installation.
Figure 5B:
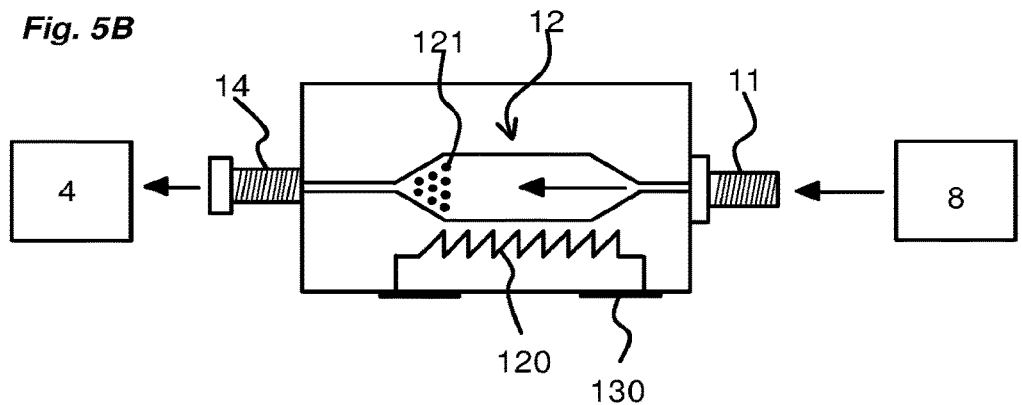

The cartridge also comprises a preconcentrator 12 housed inside its housing and connected hermetically to its fluid inlet. The preconcentrator 12 makes it possible to accumulate, using an adsorbent, the compounds to be detected that are present in the gaseous sample and makes it possible to release them by thermal desorption, under the effect of an abrupt temperature rise. An amplification of the concentration and therefore of the signal will thus be able to be obtained. As illustrated by FIGS. 5A and 5B, a preconcentrator for example consists of a silicon microcomponent filled with at least one adsorbent (for example particles of Tenax—registered trademark) and provided with a heating resistor 120 on its bottom face. Metal or silica capillaries make it possible to ensure the circulation of the gas mixture in the device. Micropillars 121 are arranged in front of the outlet of the preconcentrator to prevent the leaking of the adsorbent particles used in the cartridge.

The cartridge also comprises an electrical connector 13, for example formed by several electrical tracks or flexible blades 130 on the surface of its housing and linked on one side to the heating resistor 120 and to a temperature sensor of its preconcentrator and on the other side to an electrical power source which makes it possible to power said heating resistor 120 and said temperature sensor of the preconcentrator.

The cartridge 1 also comprises a fluid outlet 14.

The fluid outlet 14 of the cartridge can be linked to the pumping system of the analysis device 2 to ensure sampling by suction into the cartridge when the cartridge is inserted in the recess of the device.

The fluid outlet of the cartridge can be employed to discharge the compounds desorbed for analysis, to an analysis installation 4 present in a laboratory. The fluidic connection of this outlet with the adapter 3 described hereinbelow will preferentially be with small dead volume.

The cartridge 1 is positioned in the recess 200 so as to leave its fluid inlet 11 in contact with the ambient air in order to allow a gaseous sample to be taken by suction.

The analysis device 2 also comprises a fluid inlet 21, preferably with small dead volume, to which the fluid outlet 14 of the cartridge 1 is connected when the cartridge is positioned in its recess 200.

The analysis device 2 comprises a connector 22 incorporated in the housing 20 and for example formed by several electrical tracks or flexible blades formed in said recess 200 so as to connect to the connector 13 present on the cartridge 1. Each electrical track of the connector of the device comes into electrical contact with a corresponding track or flexible blade of the connector of the cartridge when the cartridge 1 is inserted into the recess 200.

The analysis device 2 also comprises an electrical power source, for example a battery 23. The latter will preferentially be removable and connected to the analysis device 2 by a connector accessible from the outside and incorporated in the housing 20 of the system. This battery 23 makes it possible to power the different elements of the device described hereinbelow, in particular its control and processing unit 24 and its pumping system, as well as the various heating solutions.

The analysis device 2 comprises a control and processing unit 24 intended to manage the operation of the device. This unit 24 is powered by said battery 23 and arranged to implement different operating modes, in particular a sampling and analysis operating mode and, if necessary, a cartridge 1 reinitialization operating mode. These operating modes will be explained hereinbelow.

The analysis device 2 comprises a pumping system powered by said battery 23.

Referring to FIG. 2, this pumping system comprises at least one first pump 27a for sucking a fluid sample into the preconcentrator 35 of the detection assembly, through the first fluid inlet IN1. This first pump 27a is connected, via a first valve V1, between the preconcentrator 35 and the column 25.

The pumping system also comprises a second pump 27b connected to the outlet of the detector 26 of the detection assembly and intended to suck the desorbed compounds into the preconcentrator 35 through the column 25 and to the detector 26, via a controlled valve V2.

The pumping system comprises a third pump 27c intended to suck a fluid sample into the sampling assembly, through the second fluid inlet IN2, via a third controlled valve V3.

Any other arrangement of the pumping system will of course be able to be envisaged. A same pump with two distinct suction circuits, using valves or check device, could notably be employed. Valves controlled by the control and processing unit 24 are of course provided to ensure the circulation of the sample in the device.

For its control, the analysis device 2 comprises one or more control members 28 incorporated in the housing and linked to inputs of its control and processing unit 24.

The analysis device 2 advantageously comprises a signaling unit, comprising for example a display 29 or other human-machine interface, and responsible for indicating to the user the state of the device and various results deriving from the analysis of the gaseous sample. The device will also be able to have communication means for sending the results through a wired or wireless link to a terminal, for example a mobile terminal. The communication link will be able to be employed bidirectionally, to send the results from the device to the terminal and to parameterize the device from the terminal (for example: setting alert thresholds—see below).

The control and processing unit 24 is configured to ensure the operation of the device.

Advantageously, the control and processing unit 24 implements a particular analysis operating mode.

In this analysis operating mode, the analysis device 2 operates as follows:
  The user generates an analysis command by action on a control member 28 of the device 2, launching the analysis operating mode of the device.
  The control and processing unit 24 opens the valve V1 and activates the first pump 27a to command the suction of a gaseous sample into the preconcentrator of the detection assembly through the first fluid inlet IN1. The valve V2 is closed.
  The preconcentrator 12 captures the targeted compounds by adsorption.
  Once the preconcentration phase is finished, the control and processing unit 24 activates the heating of the heating resistor 120 of the preconcentrator 12 so as to desorb the compounds accumulated.
  The control and processing unit 24 opens the valve V2 and activates the second pump 27b to discharge the desorbed compounds by suction to the column 25 then into the detector 26 with thermal conductivity. This discharge to the device will be performed by suction of a volume of air which carries said compounds with it. The valve V1 is closed.
  The detector 26 generates successive voltage spikes, which correspond to the passage of each compound and which are intended to be interpreted by the control and processing unit 24.
  The control and processing unit 24 analyzes the various voltage spikes obtained (chromatogram), for example by comparing them to predefined alert thresholds so as to generate or not generate an alert.
  In the event of an alert threshold being exceeded, the control and processing unit 24 immediately commands a new sampling in the sampling assembly.
  The control and processing unit 24 opens the valve V3 and activates the third pump 27c so as to suck a fluid sample into the sampling assembly, that is to say into the cartridge, through the second fluid inlet IN2.
  The cartridge will then be able to be extracted from the device for a more in-depth analysis in an installation 4 of chromatograph type present in a laboratory (see below).

The time which elapses between the first sampling for analysis by the detection assembly and the second sampling after detection of the exceeding of an alert threshold for at least one compound needs to be as short as possible in order to make it possible to perform the second sampling in conditions approximating, even identical to, those of the first sampling. This time will advantageously be less than 1 minute.

It is essential to note that the control of the sampling assembly, after the presence of an alert, is implemented automatically by the control and processing unit 24, without intervention from the user. Another option would be to issue a proposal to the user to perform the second sampling in the cartridge in case of an alert threshold being exceeded.

Said installation 4 comprises a chromatography column 40 and a detector 41. This installation will usually be dedicated to the analysis of gaseous samples taken in cartridges such as glass tubes and positioned in a suitable accommodating unit. To analyze the new sample taken, the cartridge 1 is removed from the recess 200 of the device to be placed in a specific adapter 3 which then allows the transfer of the gaseous sample taken in the cartridge to an analysis installation 4.

Figure 4:
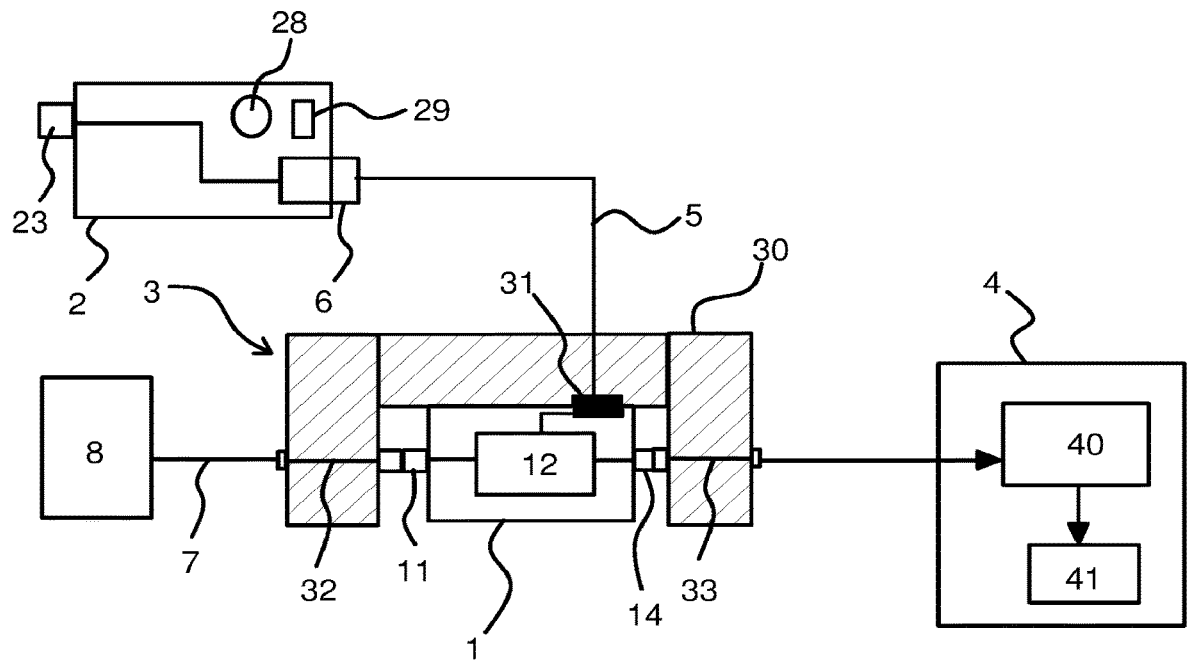
FIG. 4 schematically represents the architecture of the adapter of the invention and illustrates its principle of operation.

Thus, the adapter 3 of the invention makes it possible to position the cartridge 1 of the invention in parallel with the accommodating unit of the installation 4, without having to modify the structure of the existing installation 4. Referring to FIG. 4, this adapter 3 advantageously comprises a baseplate formed by a housing 30 defining a recess of suitable form for accommodating the cartridge 1. Said baseplate will for example be in two parts to easily insert the cartridge therein, the latter being positioned between its two parts. The adapter advantageously comprises means for assembling its two parts.

Advantageously, the analysis performed by the installation is controlled using the analysis device 2 described above. The latter is connected electrically to the adapter 3 and controls the desorption of the compounds present in the cartridge as if the cartridge 1 were in its recess 200.

The adapter 3 also comprises an electrical connector 31 incorporated in its housing 30 and linked on one side to the connector 13 of the cartridge 1 when the latter is positioned in its recess and on the other side to a power supply cable 5 linked to an electrical power source. As for the analysis device, this connector 31 advantageously comprises several electrical tracks or flexible blades each intended to cooperate with a distinct electrical track or flexible blade of the connector 13 of the cartridge 1. It is linked to the electrical power source to power the cartridge, in particular its heating resistor 120. Advantageously, the electrical power source employed is that of the analysis device of the invention, that is to say the battery 23. A contact extension block 6 is thus placed in the recess 200 of the analysis device 2 and comprises a connector provided with electrical tracks or flexible blades cooperating with the electrical tracks or flexible blades of the device 2 and linked to the battery 23. The cable 5 advantageously makes it possible to electrically link this contact block 6 to the connector 31 of the adapter.

The adapter 3 also comprises a fluid inlet 32 connected to the fluid inlet 11 of the cartridge 1 when the latter is positioned in the recess of the adapter 3 and to which is connected a pressurized vector gas source 8. This fluid inlet 32 thus has a first end-fitting of a form adapted to cooperate with the end-fitting of the fluid inlet 11 of the cartridge 1 and a second end-fitting intended to cooperate with a corresponding end-fitting produced at the end of a pipe 7 linked to said pressurized vector gas source 8 (FIG. 4). As is known, the vector gas is a mobile phase of gaseous phase chromatography and makes it possible to convey the gaseous sample along the chromatography column and the detector of the installation. The vector gas is typically helium, dihydrogen or dinitrogen. The vector gas generates no electrical signal on a chromatogram.

The adapter 3 comprises a fluid outlet 33 with small dead volume intended to cooperate on one side with the fluid outlet 14 of the cartridge when the latter is positioned in the recess of the adapter and on the other side with the installation 4 and, more specifically, with the chromatography column 40 of this installation so as to be able to directly inject into it the gaseous sample present in the cartridge 1.

For an analysis in an installation 4 present in a laboratory, the principle of operation is as follows:

The cartridge 1 comprising a gaseous sample taken on the site is positioned in the adapter 3 described above, by connecting the fluid inlet 11 of the cartridge to the fluid inlet 32 of the adapter 3 to receive vector gas from the tank 8 and by electrically powering the adapter by connecting the connector of the adapter to said contact block 6 described above and inserted into the recess 200 of the analysis device 2 of the invention.

The user generates an analysis command by action on a control member 28 of the device 2, launching the analysis operating mode of the device.

The control and processing unit 24 activates the heating of the preconcentrator present in the cartridge so as to desorb the compounds accumulated in the preconcentrator.

Once the compounds are desorbed, the latter are automatically carried to the installation 4 by the vector gas.

Using its column 40 and its detector 41, the analysis installation 4 analyzes the compounds sampled and generates an accurate chromatogram of the different compounds detected in the sample.

The reinitialization operating mode of a cartridge in the device of the invention consists in reinitializing the cartridge 1 present in the recess 200 of the device 2 and therefore in cleaning it for the latter to be able to be used again. In the reinitialization operating mode, the analysis device 2 operates as follows:

The user generates a cartridge reinitialization command by action on a control member 28 of the device.

The control and processing unit 24 commands the powering of the heating resistor 120 of the cartridge 1 and the pumping by starting up the third pump 27c, which causes the preconcentrator 12 to be cleaned by implementing a desorption. The cartridge 1 is then cleaned.

Before any re-use of the cartridge, it is necessary to wait for it to cool. Then, a new sampling can be performed in the same cartridge.

The complete solution of the invention thus offers numerous advantages, including:

It makes it possible to perform a sampling on site easily so as to obtain a rapid analysis, by the generation of an alert.

After an alert, the device quickly makes it possible to order the second sampling, even with no action from the user.

The analysis device is totally energy-independent and of little bulk, the latter operating on battery and with no vector gas source (pressurized gas cylinder). This absence of pressurized gas source reduces the maintenance needs, and makes the device advantageous for applications of continuous monitoring type.

If necessary, the device requires only a single cartridge because the latter is re-usable.

By directly connecting the cartridge to the adapter, a more in-depth analysis of a sample can be performed in a laboratory (for example on a system of GC-MS type).

The invention claimed is:

1. A device for analyzing a gaseous sample comprising a first housing and which comprises:
   a detection assembly housed in said first housing comprising a first preconcentrator configured to perform a preconcentration of compounds to be analyzed of the gaseous sample and an injection, a chromatography column configured to separate said compounds present in said gaseous sample taken in a cartridge and a detector connected at the output of said chromatography column and configured to detect the presence of said separated compounds,
   a sampling assembly comprising the cartridge that is removable relative to said first housing, said cartridge comprising a second housing enclosing a second preconcentrator configured to perform a preconcentration of the compounds to be analyzed of the gaseous sample,
   a control and processing unit housed in said first housing and configured to execute an analysis operating mode in which it is capable of generating a first command for the detection assembly to analyze a first gaseous sample through the first preconcentrator, a second command to determine the exceeding of at least one alert threshold and, if an alert threshold is exceeded, a third command for the sampling assembly to take a second gaseous sample into the second preconcentrator.

2. The device as claimed in claim 1, wherein said cartridge comprises:
   a heating resistor,
   an electrical connector connected to said heating resistor and configured to be linked to an electrical power source to power said heating resistor,
   a fluid inlet through which said gaseous sample is sucked to the interior of the cartridge,
   a fluid outlet connected to said preconcentrator to discharge the compounds to be analyzed.

3. The device as claimed in claim 2, wherein the electrical connector is formed by electrical tracks flush with said second housing.

4. The device as claimed in claim 1, wherein the second housing of the cartridge is produced in a metal material.

5. The device as claimed in claim 1, wherein said first housing has a recess configured to receive said sampling cartridge removably.

6. The device as claimed in claim 1, which comprises a pumping system arranged to suck said first gaseous sample into said detection assembly and to suck said second gaseous sample into said sampling assembly.

7. The device as claimed in claim 1, which comprises a first fluid inlet connected to the detection assembly and a second fluid inlet connected to the sampling assembly.

8. The device as claimed in claim 1, wherein said control and processing unit is configured to execute a cartridge reinitialization operating mode.

9. The device as claimed in claim 1, wherein the detector is of the type with thermal conductivity.

10. The device as claimed in claim 1, which comprises an electrical power source comprising at least one removable battery and which comprises a connector incorporated in the first housing to which said battery is connected.

11. A method for analyzing a gaseous sample implemented using an analysis device that includes a first housing and which comprises a detection assembly housed in said first housing comprising a first preconcentrator configured to perform a preconcentration of compounds to be analyzed of the gaseous sample and an injection, a chromatography column configured to separate said compounds present in said gaseous sample taken in a cartridge and a detector connected at the output of said chromatography column and configured to detect the presence of said separated compounds, a sampling assembly comprising the cartridge that is removable relative to said first housing, said cartridge comprising a second housing enclosing a second preconcentrator configured to perform a preconcentration of the compounds to be analyzed of the gaseous sample, and a control and processing unit housed in said first housing and configured to execute an analysis operating mode in which it is capable of generating a first command for the detection assembly to analyze a first gaseous sample through the first preconcentrator, a second command to determine the exceeding of at least one alert threshold and, if an alert threshold is exceeded, a third command for the sampling assembly to take a second gaseous sample into the second preconcentrator, the method comprising:

activating the detection assembly to analyze the first gaseous sample, determining an exceeding of the at least one alert threshold after analysis of said first gaseous sample; and if the alert threshold is exceeded, automatic activating the sampling assembly to take the second gaseous sample.

* * * * *